(12) United States Patent
Bordewick et al.

(10) Patent No.: US 6,341,606 B1
(45) Date of Patent: Jan. 29, 2002

(54) DISPOSABLE RESPIRATORY MASK WITH ADHESIVE SKIN INTERFACE

(75) Inventors: Steven S. Bordewick, Shoreview; Gary L. Hansen, Eden Prairie; Holly Larkin, Plymouth, all of MN (US)

(73) Assignee: Mallinckrodt, Inc., St. Louis, MO (US)

( * ) Notice: Subject to any disclaimer, the term of this patent is extended or adjusted under 35 U.S.C. 154(b) by 0 days.

(21) Appl. No.: 09/314,291

(22) Filed: May 19, 1999

(51) Int. Cl.$^7$ .................. A61M 16/00; A61M 16/06
(52) U.S. Cl. ................. 128/206.25; 128/206.12; 128/206.13; 128/206.14; 128/206.18; 128/206.19; 128/206.21; 128/206.24; 128/206.25; 128/206.28
(58) Field of Search .............. 128/205.25, 206.12, 128/206.13, 206.14, 206.18, 206.19, 206.21, 206.24, 206.25, 206.28

(56) References Cited

U.S. PATENT DOCUMENTS

| | | | |
|---|---|---|---|
| 2,921,581 A | * 1/1960 | Swearingen et al. | 128/146 |
| 3,357,426 A | 12/1967 | Cohen | |
| 5,333,607 A | * 8/1994 | Kee et al. | 128/204.18 |
| 5,357,952 A | * 10/1994 | Schuster et al. | 128/207.17 |
| 5,657,752 A | * 8/1997 | Landis et al. | 128/207.13 |
| 5,709,414 A | * 1/1998 | Bailey et al. | 285/242 |
| 5,735,270 A | * 4/1998 | Bayer | 128/206.14 |
| 5,782,236 A | * 7/1998 | Ess | 128/207.17 |
| 5,842,469 A | * 12/1998 | Rapp et al. | 128/200.24 |
| 6,119,693 A | * 9/2000 | Kwok et al. | 128/207.11 |

FOREIGN PATENT DOCUMENTS

| | | |
|---|---|---|
| EP | 0 462 701 | 12/1991 |
| EP | 0 549 299 | 6/1993 |

* cited by examiner

Primary Examiner—John G. Weiss
Assistant Examiner—Mital Patel
(74) Attorney, Agent, or Firm—Rothwell, Figg, Ernst & Manbeck, P.C.

(57) ABSTRACT

A disposable respiratory mask is provided according to the invention. The disposable respiratory mask includes a bag having a first opening and a second opening and may have an optional vent hole, adhesive strips around a perimeter of the first opening, the adhesive strips being capable of attaching the mask to a face region around a nose, an interface tube having an optional vent hole, the proximal end of the interface tube capable of being inserted into the second opening of the bag, the distal end of the interface tube capable of connecting to a gas supply hose, and a retainer ring capable of being positioned over the bag and the interface tube to hold the bag on an outer surface of the interface tube when the interface tube is inserted into the second opening of the bag, wherein a gas is supplied to the mask through the gas supply hose, with the bag being inflated by the gas and the bag is therefore positioned away from a wearer's face.

19 Claims, 5 Drawing Sheets

DISPOSABLE RESPIRATORY MASK WITH ADHESIVE SKIN INTERFACE

BACKGROUND OF THE INVENTION

1. Field of the Invention

The present invention relates generally to the field of respiratory masks.

2. Description of the Background Art

A respiratory mask is a device used to deliver a gas or gases to a patient. In its simplest form, the respiratory mask includes a face piece, an attaching means, and a gas supply hose. The respiratory mask may be used to deliver any variety of gases, including air or oxygen, and a variety of medicines or treatments.

The face piece is fitted over a nose portion of the face of the patient, and may optionally also fit over the mouth of the patient. Preferably, the fit around the edges of the face piece with the skin of the patient is substantially airtight, not allowing the supplied gas to escape. A strap or other attaching means is fitted over the head of the patient. The function of the attaching means is to hold the face piece against the face of the patient in order to deliver the gas to the patient, and also to ensure that the face piece forms a seal with the face of the patient. Constant pressure gas is therefore delivered, with the mask also including a vent hole whereby a constant pressure is maintained in the mask. This is referred to as a continuous positive airway pressure (CPAP) mask. The vent hole allows clearance of expired $CO_2$.

However, the respiratory mask of the related art has several drawbacks. First, related art respiratory masks have typically been constructed of a relatively inflexible material, such as rubber or plastic, and are therefore heavy to wear. The weight of a respiratory mask may become a major factor of wearer discomfort if the mask must be worn repetitively or for long periods of time. The weight of the mask may also affect the ease in which the mask may be positioned or retained in position. Wearing a related art respiratory mask may result in sag or slippage over time, even if the mask is not excessively heavy.

A second drawback is that the related art respiratory mask is relatively inflexible, and the seal between the face piece and a face of a patient is therefore problematic, as a patient's face may rapidly move, contract, expand, or shift as the patient's face moves under muscular control. Gaps between the mask and face may therefore appear and disappear. The application of a dosage of a gas or medicine may be affected as a result.

A third drawback of related art respiratory masks is that inflexible face pieces do not accommodate a variety of sizes of patients.

A fourth drawback is that related art devices are not disposable, and may require disinfection in order to avoid contamination between uses.

There remains a need in the art for an improved respiratory mask.

SUMMARY OF THE INVENTION

A disposable respiratory mask is provided according to the invention. The disposable respiratory mask includes a bag having a first opening and a second opening and may have an optional vent hole, adhesive strips around a perimeter of the first opening, the adhesive strips being capable of attaching the mask to a face region around a nose, an interface tube having an optional vent hole, the proximal end of the interface tube capable of being inserted into the second opening of the bag, the distal end of the interface tube capable of connecting to a gas supply hose, and a retainer ring capable of being positioned over the bag and the interface tube to hold the bag on an outer surface of the interface tube when the interface tube is inserted into the second opening of the bag, wherein a gas is supplied to the mask through the gas supply hose, with the bag being inflated by the gas and the bag is therefore positioned away from a wearer's face.

The above and other features and advantages of the present invention will be further understood from the following description of the preferred embodiment thereof, taken in conjunction with the accompanying drawings.

DETAILED DESCRIPTION OF THE PREFERRED EMBODIMENTS

Figure 1:
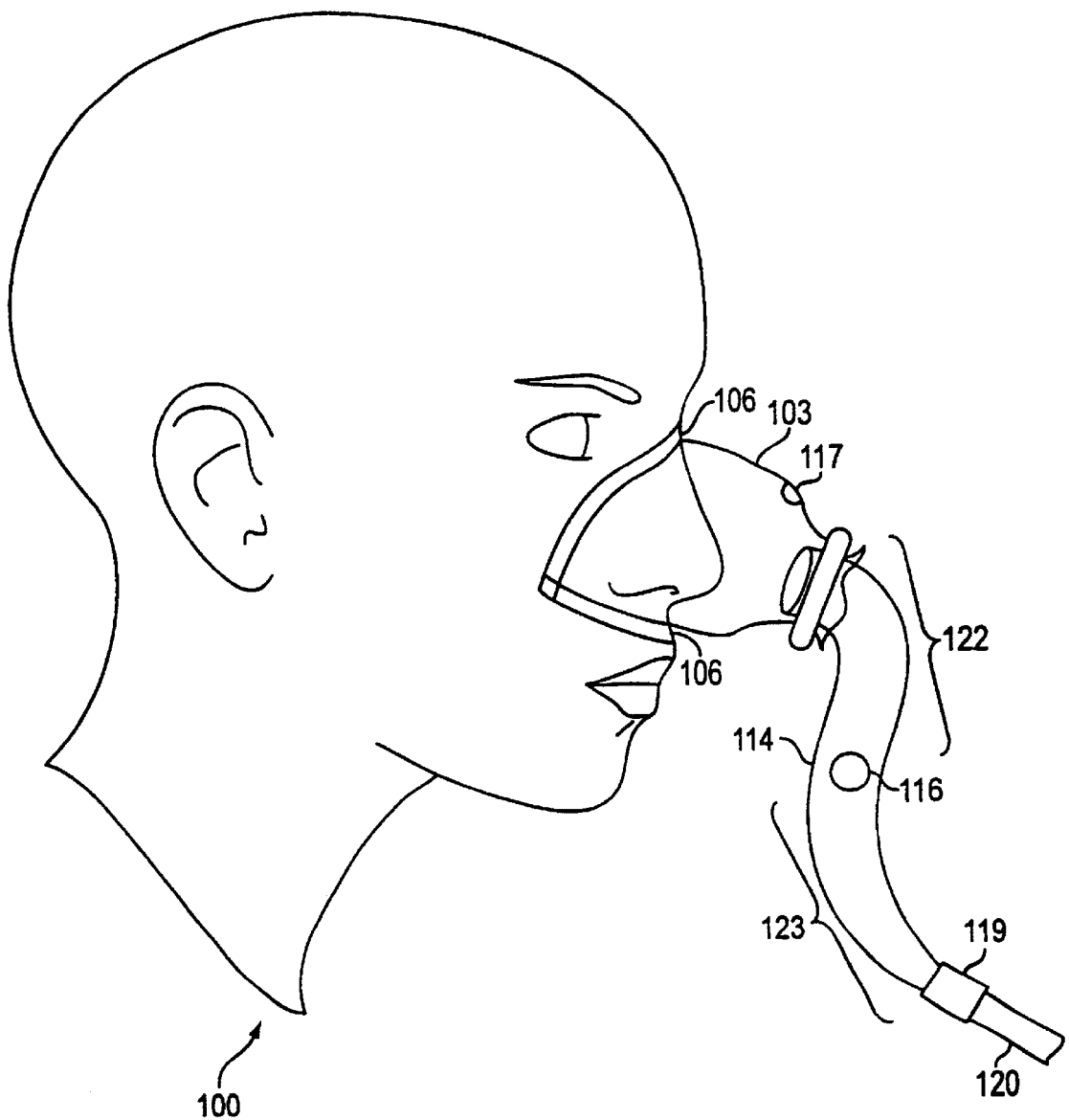
FIG. 1 shows a respiratory mask of a first embodiment of the present invention.

FIG. 1 shows a respiratory mask 100 of a first embodiment of the present invention. The respiratory mask includes a bag 103 with an optional vent hole 117, adhesive strips 106, a retainer ring 111, an interface tube 114 having an proximal end 122, a distal end 123 and an optional vent hole 116, and a swivel 119.

The adhesive strips 106 attach the bag 103 to a wearer's face, and more specifically the adhesive strips 106 removably attach the bag 103 to the wearer's face. In the preferred embodiment, the adhesive strips 106 are formed of a double-sided tape having adhesive on opposite surfaces thereof, but alternatively may be of an adhesive-impregnated foam. In yet another alternate embodiment, the adhesive strips may be a layer of adhesive deposited on the material of the bag.

The bag 103 is formed of a thin, flexible material that is substantially impervious to air or other gases. In the preferred embodiment, the bag 103 is formed of an elastomer. It is contemplated that the bag 103 may alternatively be formed of any other suitable material. The bag 103 is of a size so that a first end (the end corresponding to the adhesive strips 106) fits easily and comfortably over the nose area of a wearer. However, the bag must not be too big so as to extend excessively across the wearer's face. The bag 103 also includes a second end which is discussed below.

The interface tube 114 connects the bag 103 to an air supply. The interface tube 114 is generally tapered in size, with an proximal end 122 flaring to the greatest size. The second end of the bag 103 fits over the proximal end 122 of the interface tube 114, and the bag 103 is thereupon held in place by the retainer ring 111.

The retainer ring 111 is rolled or otherwise moved over the top of the second end of the bag 103, and traps the bag 103 onto the proximal end 122 of the interface tube 114. The bag 103 is thereby retained on the interface tube 114 by the retainer ring 111 due to the taper of the interface tube 114. In the preferred embodiment, the retainer ring 111 may be an elastic material such as a soft rubber ring, but alternatively may be formed of other materials and may be rigid and inflexible. If an elastic retainer ring 111 is employed, the retainer ring 111 may be positioned at a spot on the interface tube 114 where the inner diameter of the retainer ring 111 is less than the outer diameter of the interface tube 114, thereby stretching the retainer ring 111 and so applying a constrictive force to the bag 103 and the interface tube 114. As an additional feature, the interface tube 114 may have a circumferential groove or depression located near the upper end to provide a seat for the retainer ring 111.

The vent hole 116 and/or 117 may be included, for flushing expired $CO_2$ from the respiratory mask 100. The vent hole 116 is shown on the side of the interface tube 114, but it should be understood that the vent hole 116 may be positioned anywhere on the interface tube 114. In addition, the diameters of the vent holes 116 and/or 117 may be changed to accommodate a desired level of $CO_2$ clearance.

At the distal end 123 of the interface tube 114 is the swivel connector 119. The swivel connector 119 allows the interface tube 114 to be rotatably attached to a gas supply hose 120. The swivel connector 119 therefore allows the wearer to comfortably position the interface tube 114 to accommodate various positions, such as laying supine, laying on either side, sitting or erect.

Figure 2:
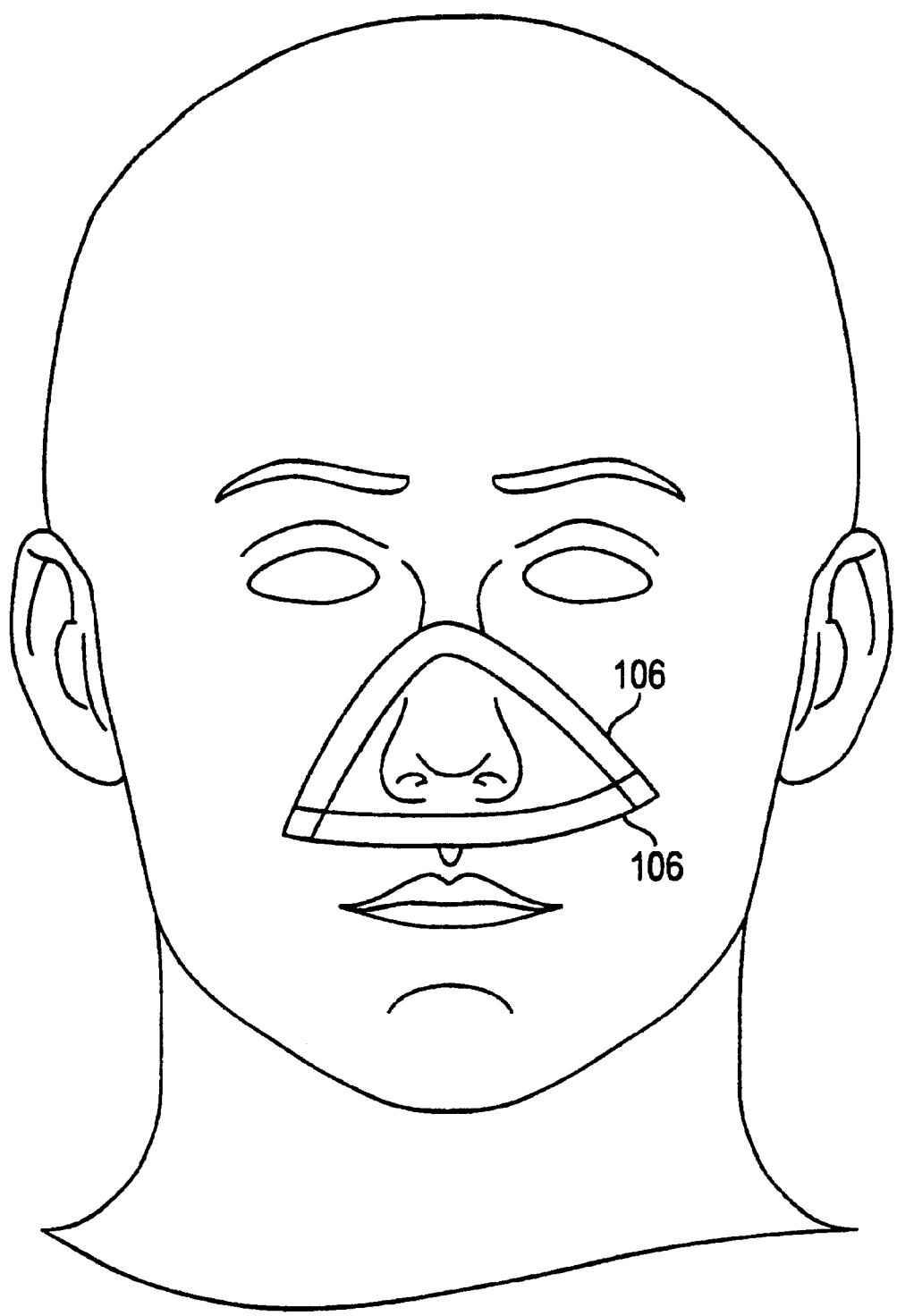
FIG. 2 shows a placement of the respiratory mask.

FIG. 2 shows a placement of the respiratory mask 100 and shows how the adhesive strips 106 are positioned around the nose and nostrils of the wearer. It should be noted that the ends of the adhesive strips 106 may overlap as shown, or may butt against each other in some manner. The adhesive strips 106 therefore accommodate faces of different sizes while retaining a substantially airtight seal (airtight defined as a barrier to any type of gas).

Figure 3:
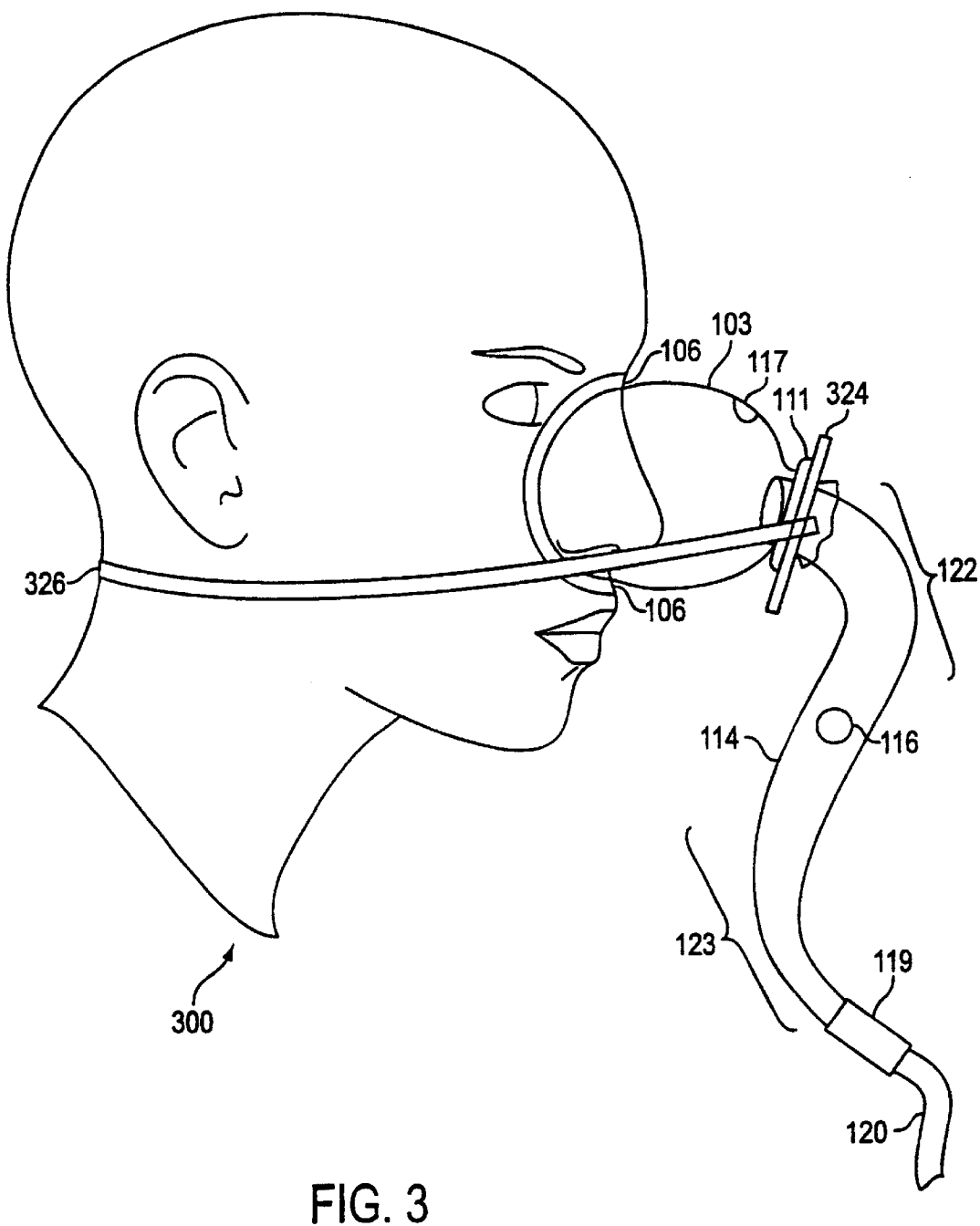
FIG. 3 shows a respiratory mask of a second embodiment.

FIG. 3 shows a second embodiment 300 of the respiratory mask of the present invention. The respiratory mask 300 includes, in addition to the components recited with respect to FIG. 2, a strap ring 324 and a strap 326.

The strap ring 324 is a ring that freely moves on the interface tube 114, but cannot escape from the proximal end 122 of the interface tube 114 due to the taper. The strap ring 324 is also held on the interface tube 114 by the retainer ring 111.

The strap 326 has ends attached to the strap ring 324, and the strap 326 may be placed around the head of the wearer. In the preferred embodiment, the strap 326 is made of an elastic material, with the tension of the strap 326 serving to hold the respiratory mask 300 in a desired position on the face of the wearer. The force produced by the strap 326 is resisted in part by the inflation of the bag 103. The strap 326 may optionally include an adjusting means (not shown) wherein the length of the strap 326 may be adjusted to accommodate wearers of different sizes.

In a variation from the first embodiment 100, the second embodiment 300 may optionally include a bag 103 of a semi-rigid plastic material, wherein the interface tube 114 is held away from the wearer's face partially by the inflation of the bag 103 and partially by a stiffness of the material of the bag 103.

Figure 4:
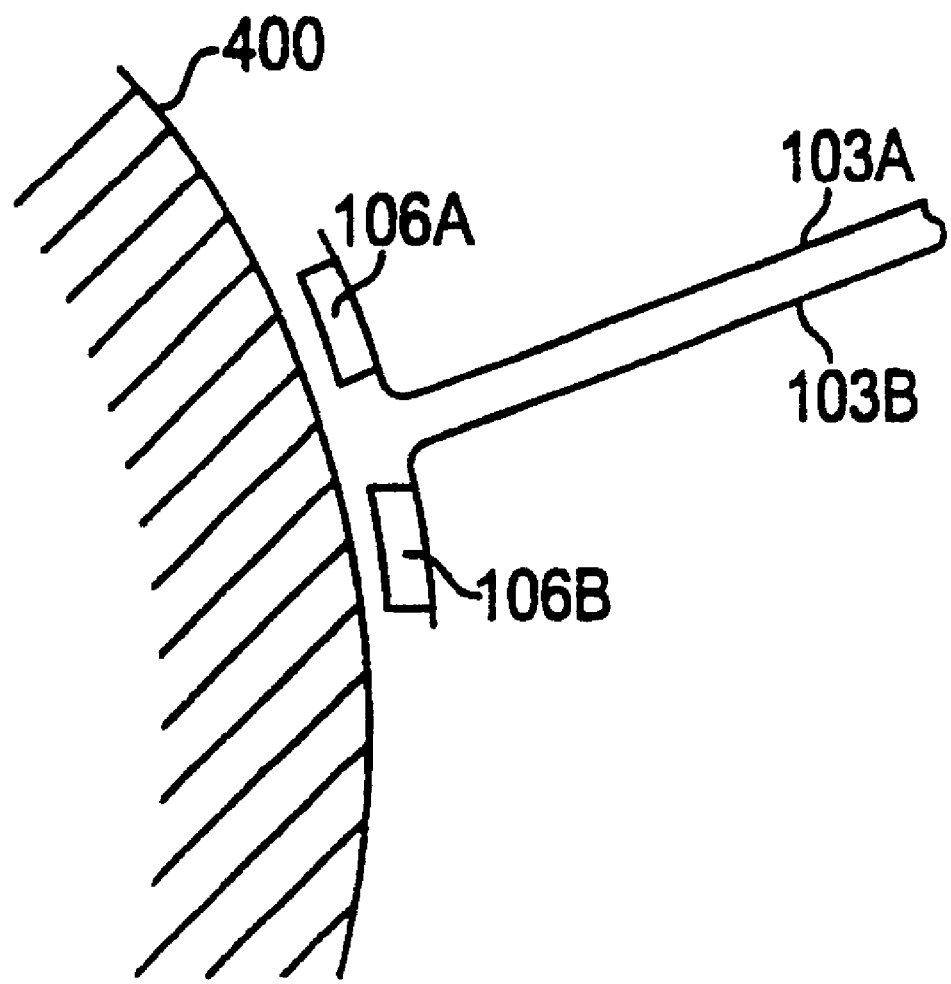
FIG. 4 shows a detail of a skin-to-mask interface.

FIG. 4 shows a detail of the attachment of the bag 103 to the skin 400 of a wearer. Here the bag 103 is formed of two plies of material, labeled 103A and 103B in the figure. Ply 103A includes an adhesive strip 106A, while ply 103B includes an adhesive strip 106B. At the skin-to-mask interface, the two plies 103A and 103B are separated and the adhesive strips 106A and 106B are brought into contact with the skin 400. Preferably the two plies 103A and 103B are bonded together, in a region outside of the adhesive strips 106A and 106B. This equalizes the shear forces to the skin and minimizes the chance of the adhesive detaching prematurely.

Figure 5:
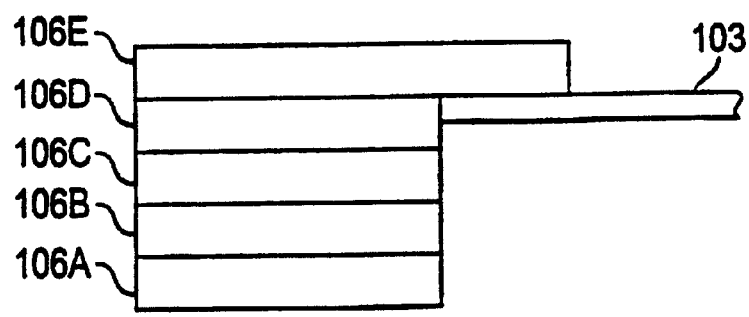
FIG. 5 shows a detail of a plurality of adhesive strips for reuse of the respiratory mask.

FIG. 5 shows a detail of an embodiment of the adhesive strips 106 wherein the adhesive strips 106 include a plurality of such strips disposed atop one another. Shown are five such strips 106A–106E, although it should be understood that any number of strips may be employed. All of the strips are adhesive in nature, with the purpose of multiple strips being that after an adhesive strip 106, such as strip 106A, has been used, it may be peeled off and discarded. Therefore, a respiratory mask employing multiple adhesive strips 106 as shown, may be used multiple times without losing effectiveness. When the last strip has been reached, such as strip 106E in this example, the disposable respirator mask has been expended and may be discarded.

Figure 6:
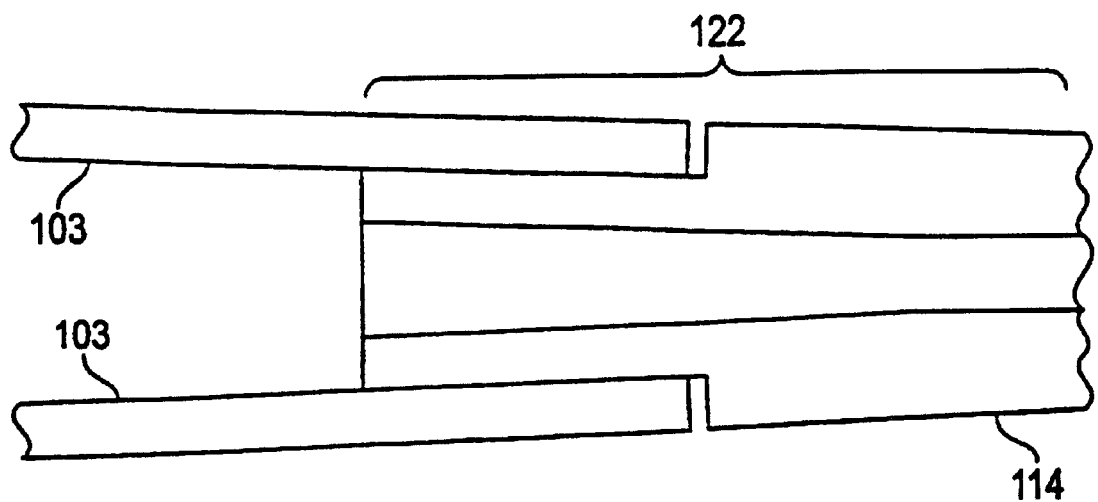
FIG. 6 shows a detail of a mating between the interface hose and a bag of the respiratory mask.

FIG. 6 shows a detail of the proximal end 122 of the interface tube 114. The figure shows the taper of the interface tube 114 at the proximal end 122, whereby the bag 103 is more readily retained on the interface tube 114. The taper also serves to limit the movement of the retainer ring 111 and the strap ring 324 (see FIG. 3).

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A disposable respiratory mask, comprising:
a bag having a first opening and a second opening;
adhesive strips around a perimeter of said first opening, said adhesive strips being capable of attaching said mask to a face region around a nose;
an interface tube having proximal and distal ends, said proximal end of said interface tube adapted for insertion into said second opening of said bag, said distal end of said interface tube adapted for connection to a gas supply hose; and
a retainer ring capable of being positioned over said bag and said interface tube to hold said bag on an outer surface of said interface tube when said interface tube is inserted into said second opening of said bag;
wherein, when a gas is supplied to said mask through a gas supply hose, said bag is inflated by said gas and said bag thereby extends away from a wearer's face.

2. The mask of claim 1 wherein said bag further includes a vent hole.

3. The mask of claim 1 wherein said interface tube further includes a vent hole.

4. The mask of claim 1, wherein said bag is disposable while said interface tube is reusable.

5. The mask of claim 1, wherein said bag is an elastomer.

6. The mask of claim 1, wherein said bag is a semi-rigid plastic.

7. The mask of claim 1, wherein said mask further includes a swivel connector at said distal end of said interface tube, said swivel connector capable of rotatably connecting said interface tube to said gas supply hose.

8. The mask of claim 1, wherein said adhesive strips further include a plurality of layers of said adhesive strips, wherein said mask can be reused by peeling off a layer of said plurality of layers of said adhesive strips.

9. A disposable respiratory mask, comprising:
a bag having a first opening and a second opening;
adhesive strips around a perimeter of said first opening, said adhesive strips being capable of attaching said mask to a face region around a nose;

an interface tube having proximal and distal ends, said proximal end of said interface tube adapted for insertion into said second opening of said bag, said distal end of said interface tube adapted for connection to a gas supply hose; and a retainer ring capable of being positioned over said bag and said interface tube to hold said bag on an outer surface of said interface tube when said interface tube is inserted into said second opening of said bag;

wherein, when a gas is supplied to said mask through a gas supply hose, said bag is inflated by said gas and said bag thereby extends away from a wearer's face;

a strap ring positioned adjacent said proximal end of said interface tube, wherein said strap ring has an inner diameter less than an outer diameter of said proximal end of said interface hose because of a taper in the interface hose; and a strap having ends attached to said strap ring and sized to fit around a wearer's head.

wherein said strap ring and said strap function to hold said mask onto said wearer's head.

10. The mask of claim 9, wherein said strap ring is cardboard.

11. The mask of claim 9, wherein said strap is elastic.

12. A disposable respiratory mask, comprising:

a bag having a first opening and a second opening;

adhesive strips around a perimeter of said first opening, said adhesive strips being capable of attaching said mask to a face region around a nose;

an interface tube having proximal and distal ends, said proximal end of said interface tube adapted for insertion into said second opening of said bag, said distal end of said interface tube adapted for connection to a gas supply hose; and a retainer ring capable of being positioned over said bag and said interface tube to hold said bag on an outer surface of said interface tube when said interface tube is inserted into said second opening of said bag;

wherein, when a gas is supplied to said mask through a gas supply hose, said bag is inflated by said gas and said bag thereby extends away from a wearer's face;

wherein said interface tube has a taper, increasing in size at said proximal end.

13. A disposable respiratory mask, comprising:

a bag having a first opening and a second opening;

adhesive strips around a perimeter of said first opening, said adhesive strips being capable of attaching said mask to a face region around a nose;

an interface tube having proximal and distal ends, said proximal end of said interface tube adapted for insertion into said second opening of said bag, said distal end of said interface tube adapted for connection to a gas supply hose; and a retainer ring capable of being positioned over said bag and said interface tube to hold said bag on an outer surface of said interface tube when said interface tube is inserted into said second opening of said bag;

wherein, when a gas is supplied to said mask through a gas supply hose, said bag is inflated by said gas and said bag thereby extends away from a wearer's face;

wherein a material of said bag is formed of two plies, with an edge of an outer ply pulled outward relative to an interior of the mask and having an adhesive strip placed adjacent an edge of said outer ply, and with an edge of an inner ply pulled inward relative to the interior of the mask and having an adhesive strip placed adjacent an edge of said inner ply, wherein each said ply is capable of adhesively contacting a face region around a nose.

14. A disposable respiratory mask, comprising:

a bag having a first opening and a second opening;

adhesive strips around a perimeter of said first opening, said adhesive strips being capable of attaching said mask to a face region around a nose;

an interface tube having proximal and distal ends, said proximal end of said interface tube adapted for insertion into said second opening of said bag, said distal end of said interface tube adapted for connection to a gas supply hose; and a retainer ring capable of being positioned over said bag and said interface tube to hold said bag on an outer surface of said interface tube when said interface tube is inserted into said second opening of said bag;

wherein, when a gas is supplied to said mask through a gas supply hose, said bag is inflated by said gas and said bag thereby extends away from a wearer's face;

wherein said retainer ring has an inner diameter less than an outer diameter of said proximal end of said interface hose.

15. A method of using a bag with first and second openings as a respiratory mask, said method comprising the steps of attaching the mask to the face of a user using adhesive strips around a perimeter of the first opening;

inserting a proximal end of an interface tube into the second opening;

moving a retainer ring to a position over the bag and the interface tube to hold the bag on an outer surface of the interface tube; and connecting a distal end of the interface tube with a gas supply hose.

16. The method of claim 15, further comprising the step of flushing expired gases from the mask via a vent hole formed in the interface tube.

17. The method of claim 15, wherein said step of connecting the interface tube with a gas supply hose is performed using a swivel connector.

18. The method of claim 15, wherein said step of attaching the mask to the face of user include attaching ends of a strap to a strap ring on the interface tube and placing the strap around the head of the user.

19. The method of claim 15, further comprising the steps of disposing of the mask and reusing the interface tube.

* * * * *